United States Patent [19]

Suzuki

[11] Patent Number: 5,004,600
[45] Date of Patent: Apr. 2, 1991

[54] DEODORIZING AGENT

[75] Inventor: Atsushi Suzuki, Kamifukuoka, Japan

[73] Assignee: Cleanlite Aire Inc., Mississauga, Canada

[21] Appl. No.: 498,664

[22] Filed: Mar. 26, 1990

Related U.S. Application Data

[63] Continuation-in-part of Ser. No. 884,137, Jul. 10, 1986, abandoned.

[30] Foreign Application Priority Data

Jul. 12, 1985 [JP] Japan .................................. 60-153738

[51] Int. Cl.$^5$ ................................................. A61L 9/04
[52] U.S. Cl. ..................................... 424/76.3; 424/76.1
[58] Field of Search .............................. 424/76.1–76.3

[56] References Cited

FOREIGN PATENT DOCUMENTS

| 0053055 | 6/1982 | European Pat. Off. | 424/76 |
|---|---|---|---|
| 48-3383 | 1/1973 | Japan | 424/76 |
| 53-101535 | 9/1978 | Japan | 424/76 |
| 55-24532 | 2/1980 | Japan | 424/76 |
| 58-10052 | 1/1983 | Japan | 424/76 |
| 58-185161 | 10/1983 | Japan | 424/76 |

OTHER PUBLICATIONS

Eggensperger et al, Chem. Abst., vol. 86, #60569c (1977).
Vickers et al, Chem. Abst., vol. 99, #92895r (1983).

*Primary Examiner*—James H. Reamer
*Attorney, Agent, or Firm*—Kenneth M. Garrett

[57] ABSTRACT

Aqueous compositions comprising glyoxal, glycol and calcium chloride used for the treatment of air to remove odors therefrom. Filters using the compositions impregnated onto substrates have a long life in use.

20 Claims, No Drawings

DEODORIZING AGENT

CROSS REFERENCE TO RELATED APPLICATION

This application is a continuation-in-part of U.S. patent application Ser. No. 884,137 filed Jul. 10, 1986 now abandoned.

FIELD OF THE INVENTION

The present invention relates to glyoxal based deodorizing compositions useful for the treatment of air for the removal therefrom of offensive odors such as are associated with active nitrogen compounds and active sulfur compounds and the like.

DESCRIPTION OF THE PRIOR ART

Glyoxal has a nature such that it chemically reacts with active nitrogen compounds such as ammonia and amines and active sulfur compounds such as hydrogen sulfide and mercaptans and various other kinds of materials having an offensive odor, and changes them to odorless compounds. Due to their nature, glyoxal based deodorizing compositions are widely used as deodorizing agents in the industrial field and in home use.

Generally speaking the prior art deodorizing compositions comprise aqueous solutions of glyoxal alone or in admixture with water soluble organic polyoxls. In Japanese Kokai 53-101535 it is indicated that aqueous solutions of glyoxal and glycols impregnated onto porous substrates may be spread so that the solution evaporates into the room atmosphere, to thereby neutralize odors. Glyoxal is classified in the Merk Index as being moderately irritating to the skin and mucous membranes, and in the Kirk Othmer Chemical Encyclopedia as potentially causing skin irritation. Accordingly, it is desirable that its release into the atmosphere be limited, particularly where individuals are likely to be exposed for long periods of time, as may occur in a domestic environment.

The prior art compositions have excellent stability and longevity when used for the deodorization of tanks of liquid such as sewage tanks and toilet bowls or the like, where they remain in solution. Where the compositions are impregnated onto substrates and exposed to the atmosphere, their activity rapidly diminishes. While I do not wish to be bound by theory, it appears that this loss in activity is primarily connected with the loss of water from the composition. At about 80% concentration of the glyoxal, this then becomes a gel, the deodorizing effectiveness of which is relatively low. Thus the prior art glyoxal based deodorizing compositions are unsuited for applications where it is desired to deodorize air for long periods of time, such as in refrigerators, toilets, patient's rooms, locker rooms, dressing rooms, and the like.

SUMMARY OF THE INVENTION

I have found that the life of the prior art glyoxal-water soluble polyol based compositions when used for atmospheric deodorization can be remarkably prolonged by the addition of calcium chloride to the compositions.

I have also found that the deodorizing compositions of the invention have an extremely low rate of release of glyoxal into the atmosphere.

In accordance with the invention, compositions useful for the treatment of air or other gases for the removal of odors therefrom comprise by weight 100 parts glyoxal, from about 35 to about 65 parts by weight of a water soluble organic polyol, and from about 60 to about 100 parts of calcium chloride, in aqueous solution.

Non-limiting examples of water soluble polyols used or described for use in prior art glyoxal based deodorizing compositions include alkylene glycols such as ethylene glycol and propylene glycol, glycerol, water soluble polymers such as polyglycols, polyvinyl alcohol and water soluble celluloses and derivatives thereof, with propylene glycol being preferred where the compositions are intended for use in the treatment of indoor air. Such polyols have a relatively low vapour pressure under normal ambient conditions. They are hydrophilic in nature and act at least in part as humectants to retain the water in the system, thereby reducing formation of the polyglyoxal gel, and so increasing the time-effectiveness of the deodorizing compositions and substrates impregnated therewith. The suitability of these and other organic water soluble polyols as known in the art will be gauged from their stability and effectiveness in reducing the evaporation of water from the system, their toxicologic properties in relation to any particular use to which the deodorizing composition may be put, and also from an economic standpoint, and it is possible that polyols other than those specifically mentioned may be preferred according to particular circumstances. It is also apparent that mixtures comprising more than one polyol may be utilized.

Typically, the blending amounts of the glyoxal, polyol and calcium chloride may be varied in accordance with the humidity and temperature at the location where the deodorizing agent is used. In general, it is preferable to increase the amount of calcium chloride where high temperature or low humidity are likely to be experienced, while it is desirable to decrease the amount of calcium where low temperature or high humidity conditions are likely.

Preferably, when the deodorizing composition is intented for use in normal domestic environments, the calcium chloride will be used in an amount within the range of about 70 to about 80 parts by weight per 100 parts by weight glyoxal, with about 75 parts being desirable. Also preferably the organic polyol will be used in an amount within the range of about 45 to about 55 parts per 100 parts by weight glyoxal, with about 50 parts being desirable.

The composition of the invention may suitably be absorbed onto inert porous substrates for use in the treatment of air, and non-limiting examples of such substrates are felt, sponge, paper and expanded minerals, all of which are known in the prior art. However, the compositions of the invention may be used for the deodorization of air and other gas streams using other known techniques for liquid-gas contact, hence their use is not limited to their being absorbed onto porous substrates.

The amount of water into which the active ingredients of the composition are dissolved is not critical and may vary within a wide range. Obviously, in view of the foregoing it will be ensured that at the lower limit the amount of water present when the compositions are put into use for deodorization will be such as to inhibit the formation of undesirable polyglyoxal gels. The upper limit of water concentration is controlled by the desired deodorizing capacity of the composition. Generally speaking approximately equal parts of water and the combined active ingredients i.e. glyoxal, polyol and calcium chloride will be well suited for a broad range of applications.

The invention will be further described in relation to a preferred embodiment, and compared to prior art compositions herein below. Such embodiment is given by way of example and is not limiting on the invention previously described.

DESCRIPTION OF THE PREFERRED EMBODIMENT

In the exemplary embodiment a deodorizing solution Sample A is blended for use under conditions of temperature and humidity such as would normally be encountered in a domestic environment. Sample A comprises 40 parts glyoxal, 30 parts calcium chloride and 50 parts ethylene glycol in 90 parts water, all by weight. In comparison Sample B the glycol was omitted and in comparison Sample C both the calcium chloride and glycol were omitted, as summarized in Table 1. Three cubes of 4 cm side were respectively impregnated with 35 g of each of Samples A, B and C, and a fourth similar cube was impregnated with water as Sample D. The cubes were exposed in a refrigerator and the weight loss of each was measured periodically, duplicate tests being summarized in Table 2.

TABLE 1

| SAM-PLE | BLENDING AMOUNT (g) | | | |
|---|---|---|---|---|
| | GLYOXAL | CALCIUM CHLORIDE | ETHYLENE GLYCOL | WATER |
| A | 40 | 30 | 20 | 90 |
| B | 40 | 30 | 0 | 90 |
| C | 40 | 0 | 0 | 120 |
| D | 0 | 0 | 0 | 100 |

TABLE 2

| | RESULTS OF MEASUREMENT OF WEIGHT DECREASE AMOUNTS (g) | | | | | | |
|---|---|---|---|---|---|---|---|
| SAMPLE | 1 day | 3 days | 10 days | 1 month | 2 months | 3 months | 6 months |
| A1 | 1.6 | 3.8 | 8.0 | 11.5 | 11.8 | 12.0 | 12.0 |
| A2 | 1.8 | 4.0 | 8.5 | 12.0 | 12.0 | 12.5 | 12.2 |
| B1 | 2.0 | 4.5 | 10.0 | 12.2 | 13.0 | 13.2 | 13.0 |
| B2 | 1.7 | 4.5 | 10.2 | 12.5 | 13.0 | 13.2 | 13.5 |
| C1 | 2.5 | 6.0 | 21.0 | 27.5 | 28.0 | 28.0 | 28.0 |
| C2 | 2.7 | 6.7 | 21.7 | 28.0 | 28.0 | 28.0 | 28.0 |
| D1 | 3.2 | 7.7 | 28.7 | 33.5 | 34.5 | 34.5 | 34.5 |
| D2 | 3.2 | 7.7 | 28.7 | 34.0 | 34.5 | 34.5 | 34.5 |

The surface of the sponges impregnated with Samples A and B remained wet throughout the six month duration of the test, whereas sponges impregnated with Samples C and D became dry within one or two months.

In a further test, filters consisting of fifty five paper tubes each having a dimension of 10×15×1 mm were respectively impregnated with 20 g of Samples A, B and C and exposed to air streams of 0.75 l/min respectively containing 50 ppm ammonia and 20 ppm hydrogen sulfide.

The effluent gas streams were tested periodically using Kitagawa detector tubes located 10 cm from the exhaust port, the results of the test being summarized in Table 3.

TABLE 3

| SAMPLE | CONCEN-TRATION AT SUCTION PORT (ppm) | RESULTS OF MEASUREMENTS OF RESIDUAL CONCENTRATIONS AT THE EXHAUST PORT (ppm) | | | | | |
|---|---|---|---|---|---|---|---|
| | | 3 days | 10 days | 1 month | 2 months | 3 months | 6 months |
| A | AMMONIA | 5 | 5 | 5 | 5 | 8 | 10 |
| B | 50 ppm | 5 | 5 | 15 | 45 | 50 | 50 |
| C | | 20 | 45 | 50 | 50 | 50 | 50 |
| A | HYDROGEN | 2 | 2 | 2 | 2 | 2 | 2 |
| B | SULFIDE | 2 | 2 | 4 | 15 | 20 | 20 |
| C | 20 ppm | 10 | 15 | 20 | 20 | 20 | 20 |

The filter impregnated with Sample A (the deodorizing fluid of the invention) still maintains its deodorizing capability even after six months have elapsed. On the other hand, the filters impregnated with the comparison deodorizing fluids Samples B and C completely lost their deodorizing capability. Thus, the deodorizing fluid of the invention exhibited excellent results in terms of the duration of the deodorizing effect.

A further comparison Sample E was prepared comprising by weight 40 parts glyoxal, 20 parts by weight ehtylene glycol and 90 parts by weight water. The second of the above tests was repeated, although over a shorter duration of time, comparing the deodorizing effectiveness of the foregoing Samples A, B and C with that of Sample E, the results of the tests being summarized in Table 4.

TABLE 4

| Sample | | Result of measurements of residual concentrations at the exhaust port (ppm) | | |
|---|---|---|---|---|
| | | 3 days | 10 days | 1 month |
| A | ammonia | 5 | 5 | 5 |
| B | 50 ppm | 5 | 5 | 15 |
| C | | 20 | 35 | 50 |
| D | | 5 | 15 | 25 |
| A | Hydrogen | 2 | 2 | 2 |
| B | sulfide | 2 | 2 | 5 |
| C | 20 ppm | 8 | 15 | 20 |
| D | | 2 | 5 | 12 |

As may be seen from Table 4, the percentage removal of ammonia and hydrogen sulfide from the test gases was 90% over a period of one month when using the composition of the invention. In comparison the percentage removal of ammonia was only 50%, and of hydrogen sulfide only 40% at the end of the this period when using comparison Sample E, notwithstanding the fact that the concentration of glyoxal in Sample E was somewhat higher than in Sample A. Moreover, it will be appreciated that the odor removing capability of Sample E rapidly diminished over the duration of the test, whereby after only one month's exposure it was inferior to the activity of Sample A after six month's exposure, as seen from a comparison of Tables 3 and 4.

When propylene glycol is substituted for ethylene glycol in the above tests comparable results are obtained.

In a further test to measure the release of glyoxal from the deodorizing composition of the invention 100 g of Sample A is impregnated onto an equal weight of a substrate of expanded mineral (obsidian) having a bulk density of about 0.3 g/ml to form a filter medium. A filter cartridge containing 150 g of this medium is exposed to an air stream at 40° C. for a period of 10 days. The effluent gas is filtered through SEP-PAK TM cartridges coated with 2, 4 dinitro-phenylhydrazine, and the cartridges eluted with acetonitrile and analyzed by HPLC. The cummulative amount of glyoxal detached in the effluent stream over this 10 day period is $80 \times 10^6$ g. A filter cartridge containing 150 g of filter medium is normally recommended for use in a domestic environment in a room having a volume of about 30 m$^3$. Persons skilled in the art will recongnize that the concentration of glyoxal released into the atmosphere of such room would be without effect on such odors as ammonia and hydrogen sulfide and their commonly encountered simple organic odor causing derivatives.

It will be apparent that many changes may be made to the illustrative embodiment, while falling within the scope of the invention and it is intended that all such changes be covered by the claims appended hereto.

I claim:

1. A composition useful for the treatment of air for the deodorization thereof comprising 100 parts by weight glyoxal, from about 35 to about 65 parts by weight of an organic water soluble polyol and from about 60 to about 100 parts by weight of calcium chloride, in aqueous solution.

2. Deodorizing compositions as defined in claim 1, wherein said organic water soluble polyol is selected from the group consisting of ethylene glycol, propylene glycol, glycerol, water soluble polyvinyl alcohol, water soluble polyglycols and water soluble cellulose material.

3. Deodorizing compositions as defined in claim 1, wherein said organic water soluble polyol is selected from ethylene glycol and propylene glycol.

4. A substrate impregnated with the deodorizing composition of claim 1.

5. A substrate impregnated with the deodorizing composition of claim 2.

6. A substrate impregnated with the deodorizing composition of claim 3.

7. A substrate impregnated with the composition of claim 1, wherein said polyol is ethylene glycol.

8. A substrate impregnated with the composition of claim 1, wherein said polyol is propylene glycol.

9. Deodorizing compositions as defined in claim 1, wherein said aqueous solution comprises about 50 percent water by weight of the total weight of said composition.

10. Deodorizing compositions as defined in claim 9, wherein said polyol is selected from the group consisting of ethylene glycol, propylene glycol and glycerol.

11. Deodorizing compositions as defined in claim 9 impregnated onto a substrate.

12. Deodorizing compositions as defined in claim 8 impregnated onto a substrate.

13. Deodorizing compositions as defined in claim 7 impregnated onto an inert absorbent substrate selected from the group consisting of felt, sponge and paper.

14. Deodorizing compositions as defined in claim 8 impregnated onto an inert absorbent substrate selected from the group consisting of felt, sponge and paper.

15. A deodorizing composition useful for the treatment of air for the deodorization thereof comprising by weight about 40 parts of glyoxal, about 30 parts of calcium chloride, about 20 parts of a polyol selected from the group consisting of ehtylene glycol and propylene glycol, in aqueous solution.

16. A deodorizing composition as defined in claim 11 when impregnated onto a substrate.

17. A deodorizing composition as defined in claim 15, wherein said polyol is propylene glycol.

18. A deodorizing composition as defined in claim 15, wherein said polyol is ethylen glycol.

19. A deodorizing composition as defined in claim 17 when impregnated onto a substrate.

20. A deodorizing composition as defined in claim 19 when impregnated onto a substrate.

* * * * *